US008957004B2

(12) United States Patent
Chourey et al.

(10) Patent No.: US 8,957,004 B2
(45) Date of Patent: Feb. 17, 2015

(54) AERATED SOAP BARS

(75) Inventors: Ankur Chourey, Thane (IN); Camile Florido, Valinhos (BR); Sergio Roberto Leopoldino, São Paulo (BR); Edirlei Roberto Magon, Valinhos (BR); André Messias Krell Pedro, São Paulo (BR); Anal Pushkarna, Mumbai (IN); Angelica Marques Rodriques, Valinhos (BR)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 14/004,218

(22) PCT Filed: Jan. 27, 2012

(86) PCT No.: PCT/EP2012/051326

§ 371 (c)(1), (2), (4) Date: Nov. 12, 2013

(87) PCT Pub. No.: WO2012/123157

PCT Pub. Date: Sep. 20, 2012

(65) Prior Publication Data

US 2014/0053508 A1 Feb. 27, 2014

(30) Foreign Application Priority Data

Mar. 16, 2011 (IN) ........................... 744/MUM/2011
Jun. 28, 2011 (EP) ..................................... 11171615

(51) Int. Cl.

| | |
|---|---|
| ***A61K 8/00*** | (2006.01) |
| ***C11D 17/00*** | (2006.01) |
| ***C11D 3/04*** | (2006.01) |
| ***C11D 3/22*** | (2006.01) |
| ***C11D 3/37*** | (2006.01) |
| ***C11D 9/10*** | (2006.01) |
| ***C11D 9/22*** | (2006.01) |
| ***C11D 10/04*** | (2006.01) |
| ***C11D 13/16*** | (2006.01) |
| ***C11D 17/02*** | (2006.01) |
| ***B65B 3/04*** | (2006.01) |

(52) U.S. Cl.

CPC ............ *C11D 17/0047* (2013.01); *C11D 3/046* (2013.01); *C11D 3/225* (2013.01); *C11D 3/3761* (2013.01); *C11D 9/10* (2013.01); *C11D 9/225* (2013.01); *C11D 10/04* (2013.01); *C11D 13/16* (2013.01); *C11D 17/02* (2013.01); *B65B 3/04* (2013.01)

USPC ............ 510/141; 510/143; 510/152; 510/475

(58) Field of Classification Search

None

See application file for complete search history.

(56) References Cited

U.S. PATENT DOCUMENTS

| | | | | |
|---|---|---|---|---|
| 2,798,053 | A | 7/1957 | Brown | |
| 4,828,752 | A | 5/1989 | Nagarajan | |
| 5,262,079 | A | 11/1993 | Kacher et al. | |
| 5,720,961 | A | 2/1998 | Fowler | |
| 5,972,860 | A | 10/1999 | Eshita | |
| 6,770,606 | B2 | 8/2004 | Koduvely | |
| 7,427,585 | B2 | 9/2008 | Kuroda | |
| 2004/0157756 | A1 * | 8/2004 | Kuroda | 510/141 |
| 2006/0052263 | A1 | 3/2006 | Roreger | |
| 2006/0276365 | A1 | 12/2006 | Mhatre | |

FOREIGN PATENT DOCUMENTS

| | | |
|---|---|---|
| CN | 1057481 | 1/1992 |
| CN | 101554357 | 10/2009 |
| WO | WO0283832 A1 | 3/2006 |

OTHER PUBLICATIONS

PCT International Search Report in PCT application PCT/EP2012/051326 dated May 7, 2012 with Written Opinion.
European Search Report in EP application EP 11 17 1615 dated Sep. 22, 2011.
M-Hollstein et al., Anufacture and properties of synthesized toilet soaps, Household Chemistry (1986) vol. 3, p. 38-43, nma.
M-Hollstein et al., Anufacture and properties of synthesized toilet soaps (English Translation), Household Chemistry (1986) vol. 3, p. 38-43, nma.

* cited by examiner

*Primary Examiner* — Necholus Ogden, Jr.
(74) *Attorney, Agent, or Firm* — Greenberg Traurig, LLP

(57) ABSTRACT

The invention relates to aerated soap bars. Generally, it is difficult to get aerated soap bars with the right level of aeration, because high viscosity of the molten soap mass sometimes makes it difficult to aerate it to the desired extent. The size and movement of air bubbles also play important roles. Bars with larger air bubbles have lower mechanical strength. We have determined that use of acrylates or cellulose ethers in aerated soap bars lead to bars with acceptable rate of wear, mush and lower density. The soaps also have a higher and more uniform air incorporation and better air retention. Disclosed are aerated soap bars having density from 0.2 to 0.99 g/cm$^3$, comprising: (i) 20 to 80 wt % soap; (ii) 2 to 40 wt % polyol; (iii) 5 to 50% water; and, (iv) 0.5 to 5 wt % electrolyte; wherein the bars comprise 0.1 to 5 wt % polymer selected from acrylates or cellulose ethers.

10 Claims, No Drawings

AERATED SOAP BARS

The present invention relates to aerated soap bars.

Soap bars with low density (less than 1 g/$cm^3$) are generally made by aerating molten soap mass and solidifying the mass.

Generally, it is difficult to get aerated soap bars with the right level of aeration, because high viscosity of the molten soap mass sometimes makes it difficult to aerate it to the desired extent. On the other hand, if the viscosity of the molten mass is too low, the bars do not have sufficient mechanical strength. The size and movement of air bubbles also play important roles. Bars with larger air bubbles have lower mechanical strength. As the molten soap mass solidifies, the air bubbles rise upwards, but at different speeds. This may lead to bars with non-uniform density.

US 2004/157756 A (Kao Corporation) discloses framed soap bars having water, 20 to 60 wt % soap, 0.1 to 5 wt % sodium chloride, 0.1 to 5 wt % sodium sulfate and 5 to 30% polyols. The combined use of sodium chloride and sodium sulfate as inorganic salts in particular proportions make it possible to provide framed bars which solidify faster upon production. The bars have higher hardness and foamability. This application discloses that the molten soap mass may also be aerated. This application also discloses that 0.001 to 5 wt % of a high-molecular compound such as high polymerization-degree polyethylene glycol, a cationic polymer, cellulose, hydroxymethylcellulose, hydroxyethylcellulose, hydroxypropylcellulose, carboxymethylcellulose, or methylcellulose with preference for polyethylene glycol may be added for foam smoothness. While there is no suggestion to include acrylates for any benefit, there is also no suggestion that cellulose ethers provide lower wear, mush, lower density, uniform air incorporation and better air retention.

We have determined that use of acrylates or cellulose ethers in aerated soap bars lead to bars with acceptable rate of wear, mush and lower density. The soaps also have a higher and more uniform air incorporation and better air retention.

According to one aspect, the invention provides aerated soap bars having density from 0.2 to 0.99 g/$cm^3$, the bars comprising:

(i) 20 to 80 wt % soap;
(ii) 2 to 40 wt % polyol;
(iii) 5 to 50% water; and,
(iv) 0.5 to 5 wt % electrolyte, wherein the bars include 0.1 to 5 wt % polymer selected from acrylates or cellulose ethers.

According to a second aspect, the invention provides a process of preparing aerated soap bars, said process comprising the steps of:

(i) mixing 20 to 80 parts soap, 2 to 40 parts polyol, 5 to 50 parts water, 0.5 to 5 parts electrolyte, and 0.1 to 5 parts polymer selected from acrylates or cellulose ethers, to obtain a mixture;
(ii) heating the mixture to 50 to 95° C. to obtain a molten soap mass;
(iii) aerating the molten soap mass; and,
(iv) cooling the aerated molten soap mass to obtain aerated soap bars having density from 0.2 to 0.99 g/$cm^3$.

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

Except in the operating and comparative examples, or where otherwise explicitly indicated, all numbers in this description indicating amounts of material ought to be understood as modified by the word "about".

In specifying any range of concentration or amount, any particular upper concentration can be associated with any particular lower concentration or amount.

The terms weight percent, percent by weight, % by weight, wt %, and the like are synonyms that refer to the concentration of a substance as the weight of that substance divided by the weight of the composition and multiplied by 100.

As used in this specification and the appended claims, the singular forms "a", "an", and "the" include plural referents unless the content clearly dictates otherwise. Thus, for example, reference to a composition containing "a compound" includes a mixture of two or more compounds. As used in this specification and the appended claims, the term "or" is generally employed in its sense including "and/or" unless the content clearly dictates otherwise.

For better understanding of the invention, reference should be made to the following detailed description of preferred embodiments.

According to one aspect the invention provides aerated soap bars having density from 0.2 to 0.99 g/$cm^3$, the bars comprising:

(i) 20 to 80 wt % soap;
(ii) 2 to 40 wt % polyol;
(iii) 5 to 50% water; and,
(iv) 0.5 to 5 wt % electrolyte, wherein the bars include 0.1 to 5 wt % polymer selected from acrylates or cellulose ethers.

The aerated soap bars include 20 to 80 wt % soap. Preferred soap bars include 30 to 70 wt % soap; more preferably 35 to 65 wt % soap. Most preferred aerated soap bars have 40 to 60 wt % soap.

The term "soap" means salts of fatty acids, preferably alkali metal salts of fatty acids. The soap is preferably a $C_8$ to $C_{22}$ soap, more preferably a $C_{10}$ to $C_{18}$ soap. It is particularly preferred that $C_{12}$ to $C_{14}$ soap is at least 30%, more preferably at least 40% and most preferably at least 50% of the total soap content. The cation of the soap may be an alkali metal, alkaline earth metal or ammonium ion. Preferably, the cation is selected from sodium, potassium or ammonium. More preferably the cation is sodium or potassium. The soap may be saturated or unsaturated. Saturated soaps are preferred over unsaturated soaps, as the former are more stable. The oil or fatty acids may be of vegetable or animal origin.

The soap may be obtained by saponification of oil, fat or a fatty acid. The fats or oils generally used in soap manufacture may be selected from tallow, tallow stearins, palm oil, palm stearins, soya bean oil, fish oil, castor oil, rice bran oil, sunflower oil, coconut oil, babassu oil, and palm kernel oil. The fatty acids may originate from oils/fats selected from coconut, rice bran, groundnut, tallow, palm, palm kernel, cotton seed, soya bean or castor oil. The fatty acid soaps may also be synthetically prepared (e.g. by the oxidation of petroleum or by the hydrogenation of carbon monoxide by the Fischer-Tropsch process). Resin acids, such as those present in tall oil, may be used. Naphthenic acids may also be used.

Tallow fatty acids can be derived from various animal sources.

It generally includes about 1 to 8% myristic acid, about 21 to 32% palmitic acid, about 14 to 31% stearic acid, about 0 to 4% palm itoleic acid, about 36 to 50% oleic acid and about 0 to 5% linoleic acid. Other similar mixtures, such as those derived from palm oil and those derived from animal tallow and lard, may also be used.

A typical fatty acid blend contains 5 to 30% coconut fatty acids and 70 to 95% fatty acids from hardened rice bran oil.

The term water-soluble soap wherever used in this description means soap having solubility greater than 2 g/100 g water at 25° C. Preferred soap bars include at least 30%, more preferably at least 40% and most preferably at least 50% by weight water-soluble soap, of the total soap content.

Preferred soap bars include a commercially available 20:80 mixture of sodium palm kernelate and sodium palmate. The mixture has about 82% soap, 1% sodium chloride and 17% water (moisture).

In addition to soaps, preferred soap bars may also include some fatty acids. The fatty acids may have carbon chain length from $C_8$ to $C_{22}$, more preferably $C_{16}$ to $C_{18}$. Preferred bars include 0.1 wt % to 10 wt %, more preferably 0.5 wt % to 8 wt % and most preferably 1 to 5 wt % fatty acids. Bars with higher amount of fatty acids may be softer. It is preferred that these fatty acids are added after the aeration step. The fatty acids improve the quantity and quality of the lather. Fatty acids also provide an emollient effect which tends to soften the skin or otherwise improve feel-on-skin characteristics and scavenge any excess alkalinity.

The fatty acids may be added into the soap mixture either prior to, or simultaneously with high-shear mixing step used to form the aerated bars. High-shear may facilitate uniform distribution of the fatty acid in the aerated soap bars. The fatty acids may be added subsequent to the high-shear mixing step if other mixing means are used. It is preferred that the fatty acids are added to the molten soap mass during the initial crutching stage.

Alternatively, the fatty acids may be introduced prior to or during the aeration stage when perfume and other additives are generally added. The fatty acids may also be introduced as a prepared mixture of soaps and fatty acids, such as an acid-reacting mixture of soaps and fatty acids prepared by under-neutralization during the soap making process.

Preferred aerated soap bars have 0.1 to 10 wt % fatty acids, more preferably having melting point greater than 50° C. More preferred bars have 1 to 3 wt % fatty acids with melting point greater than 50° C. Without wishing to be bound by theory it is believed that such fatty acids entrap the air in a better way, when compared to fatty acids with lower melting point. Such preferred fatty acids includes lauric acid, stearic acid, palmitic acid or a mixture thereof.

The term total fatty matter, usually abbreviated to TFM, is used to denote the percentage by weight of fatty acid and triglyceride residues present in soap bars without taking into account the accompanying cations.

For a soap having 18 carbon atoms, an accompanying sodium cation will generally amount to about 8% by weight.

The TFM of preferred aerated soap bars is 40 to 80%.

The fatty acid content of the final soap so obtained is known as the total fatty matter (TFM), and can vary between 40 and 80%. The total fatty matter will include free fatty acids, when present.

The term polyol means polyhydric alcohol. The aerated bars include 2 to 40 wt %, more preferably 4 to 30 wt %, and most preferably 5 to 30 wt % polyol. Particularly preferred aerated bars include 10 to 30 wt % polyol.

Preferred polyols include glycerol, sorbitol, mannitol, alkylene glycol and polyalkylene glycol, such as polyethylene glycol. When the polyol or a part of it is a polyalkylene glycol, it is preferred that its molecular weight is 500 to 10000 Daltons. Glycerol (also known as glycerine) and sorbitol are particularly preferred. Glycerol is most preferred. Sorbitol may be used instead of glycerol. Polyols increase hardness of the aerated bars. It is believed that polyols are able to hold the soap mass in a better way and give them definite shape. Some polyols may have some amount of water. For example, commercially available glycerol and sorbitol do contain water.

The aerated soap bars include 0.5 wt % to 5 wt % electrolyte. Preferred electrolytes include chlorides, sulphates and phosphates of alkali metals or alkaline earth metals. Without wishing to be bound by theory it is believed that electrolytes help to structure the solidified aerated soap mass and also increase the viscosity of the molten mass by common ion effect. Comparative aerated soap bars without any electrolyte were found to be softer. Sodium chloride is the most preferred electrolyte, more preferably at 0.6 to 3.6 wt %, and most preferably at 1.5 to 3.6 wt %.

The aerated soap bars include 5 to 50 wt % water; preferably 20 to 50 wt % water. More preferred bars include 20 to 40 wt %, while most preferred bars include 30 to 40 wt % water. The total water includes water present in raw materials such as sorbitol.

In addition to 20 to 80 wt % soap; preferred aerated soap bars include 1 to 30 wt %, more preferably 3 to 25 wt %, and most preferably 5 to 20 wt % non-soap surfactant selected from anionic, nonionic, cationic or zwitterionic surfactants. More preferred soap bars include anionic or nonionic surfactants. Particularly preferred soap bars include anionic surfactants. Non-soap surfactants may be included in bars for higher lather or mildness.

Suitable examples of non-soap surfactants may be found in the well-known textbooks "Surface Active Agents", Volume I by Schwartz and Perry and "Surface Active Agents and Detergents", Volume II by Schwartz, Perry and Berch or "Handbook of Surfactants", M. R. Porter, Blackie Publishers, 1991.

Sodium lauryl sulphate is a particularly preferred non-soap surfactant.

The aerated soap bars include 0.1 to 5 wt % polymer selected from acrylates or cellulose ethers. Preferred acrylates include cross-linked acrylates, polyacrylic acids or sodium polyacrylates. Preferred cellulose ethers include carboxymethyl celluloses or hydroxyalkyl celluloses. A combination of these polymers may also be used, provided the total amount of polymers does not exceed 5 wt %.

Preferred bars include 0.1 to 3% acrylates. More preferred bars include 0.15 to 1% acrylates. Examples of acrylate polymers include polymers and copolymers of acrylic acid cross-linked with polyallylsucrose as described in U.S. Pat. No. 2,798,053, which is herein incorporated by reference. Other examples include polyacrylates, acrylate copolymers or alkali swellable emulsion acrylate copolymers (e.g., ACULYN® 33 Ex. Rohm and Haas; CARBOPOL® Aqua SF-1 Ex. Lubrizol Inc.), hydrophobically modified alkali swellable copolymers (e.g., ACULYN® 22, ACULYN® 28 and ACULYN® 38 ex. Rohm and Haas). Commercially available cross-linked homopolymers of acrylic acid include CARBOPOL® 934, 940, 941, 956, 980 and 996 carbomers available from Lubrizol Inc. Other commercially available cross-linked acrylic acid copolymers include the CARBOPOL® Ultrez grade series (Ultre® 10, 20 and 21) and the ETD series (ETD 2020 and 2050) available from Lubrizol Inc.

CARBOPOL® Aqua SF-1 is a particularly preferred acrylate. This compound is a slightly cross-linked, alkali-swellable acrylate copolymer which has three structural units; one or more carboxylic acid monomers having 3 to 10 carbon atoms, one or more vinyl monomers and, one or more mono- or polyunsaturated monomers.

Preferred bars include 0.1 to 3 wt % cellulose ethers. More preferred bars include 0.1 to 1% cellulose ethers. Preferred cellulose ethers are selected from alkyl celluloses, hydroxyalkyl celluloses and carboxyalkyl celluloses. More preferred bars include hydroxyalkyl celluloses or carboxyalkyl celluloses and particularly preferred bars include carboxyalkyl cellulose.

Preferred hydroxyalkyl cellulose includes hydroxymethyl cellulose, hydroxyethyl cellulose, hydroxypropyl cellulose and ethyl hydroxyethyl cellulose. Preferred carboxyalkyl cellulose includes carboxymethyl cellulose. It is particularly preferred that the carboxymethyl cellulose is in form of sodium salt of carboxymethyl cellulose.

In addition to the materials which have been described already, preferred aerated bars may include one or more of the following materials.

Preferred aerated soap bars may include 0.1 to 40 wt % organic materials, more preferably 5 to 25 wt % and most preferably 5 to 15 wt % organic materials. The materials may be particulate or non-particulate and may be selected from starch, cellulose, or wax. Particulate materials include cellulose and starch. Non-particulate materials include wax and polyalkyleneglycols.

Preferred bars include 0.1 to 5 wt % cellulose. More preferred bars include 0.1 to 2 wt %, and most preferred bars include 0.1 to 1 wt % cellulose.

Microcrystalline cellulose is particularly preferred. A preferred commercially available microcrystalline cellulose is supplied by FMC Biopolymer (Brazil) under the trade name AVICEL® GP 1030 but other commercially available materials having similar characteristics may also be used.

In addition to, or instead of cellulose, preferred aerated bars may include 5 to 30 wt %, starch, more preferably 15 to 30 wt % starch and most preferably 15 to 20 wt % starch. Natural raw starch or pre-gelatinized starch may be used. Raw starch is preferred.

Preferred wax materials includes paraffin wax and microcrystalline wax. When polyalkyleneglycols are used, preferred bars may include 0.01 to 5 wt % polyalkyleneglycols, more preferably 0.05 to 1 wt % and most preferably 0.1 to 0.6 wt %. Suitable examples include polyethyleneglycol and polypropyleneglycol. A preferred commercial product is POLYOX® sold by The Dow Chemical Company.

Preferred aerated bars may also include 1 to 50 wt % inorganic particulate materials. More preferred bars include 1 to 35 wt %, and further preferred bars include 1 to 45 wt % inorganic particulate materials. Particularly preferred bars include 5 to 30 wt % inorganic particulate materials. It is believed that the material further stabilizes the air in the molten soap mass.

The inorganic particulate materials should not be perceived as scratchy or granular and thus should have particle size preferably less than 300 μm, more preferably less than 100 μm and most preferably less than 50 μm. Preferred inorganic particulate materials include talc, calcium carbonate, magnesium carbonate, clays and mixtures thereof.

China clay is particularly preferred clay. Examples of other inorganic particulate materials include alumino silicates, aluminates, silicates, phosphates, insoluble sulphates, and borates.

A particularly preferred combination is of talc and starch, more preferably at ratios from 1:1 to 1:6. Preferred aerated soap bars with talc and starch have particularly good physical properties.

The aerated soap bars may optionally have one or more further optional ingredients. These include silicone compounds such as silicone surfactants like DC3225C™ (Dow Corning) and/or silicone emollients, silicone oil (DC-200™ Ex-Dow Corning) may also be included. Sun-screens such as 4-tertiary butyl-4'-methoxy dibenzoylmethane (available under the trade name PARSOL®1789 from Givaudan) or 2-ethyl hexyl methoxy cinnamate (available under the trade name PARSOL®MCX from Givaudan) or other UV-A and UV-B sun-screens may be used. Preferred aerated soap bars also include perfume. Such perfume may be in the form of neat oils, or encapsulated in a carrier such as starch or melamine. Such encapsulated perfumes are available from perfume houses like Firmenich, IFF and Givaudan.

Density of the aerated soap bars is 0.2 to 0.99 $g/cm^3$, more preferably 0.3 to 0.95 $g/cm^3$, and most preferably 0.4 to 0.8 $g/cm^3$. The density of non-aerated soap bars is greater than 1, and it is an essential that the bar is aerated in order to achieve the density of 0.2 to 0.99 $g/cm^3$. Density may be measured by any known means.

In accordance with another aspect the invention provides a process of preparing aerated soap bars, the process having the steps of:

(i) mixing 20 to 80 parts soap, 2 to 40 parts polyol, 5 to 50 parts water, 0.5 to 5 parts electrolyte, and 0.1 to 5 parts polymer selected from acrylates or cellulose ethers, to obtain a mixture;
(ii) heating the mixture to 50 to 95° C. to obtain a molten soap mass;
(iii) aerating the molten soap mass; and,
(iv) cooling the aerated molten soap mass, to obtain aerated soap bars having density from 0.2 to 0.99 $g/cm^3$.

In a preferred process, the molten soap mass is stored in a container, and a part of the molten soap mass is pumped out and aerated. Further preferably, the aerated molten soap mass is mixed in a homogenizer, and returned to the container, or another container.

It is preferred that the soap is melted by heating, followed by addition of the polyol, water and polymer. Alternatively the entire composition may be heated to get the molten mass.

The equipment used to prepare the hot molten mass is typically a cylindrical vessel of appropriate depth with a flat or a dished bottom. It preferably has a proper top enclosure to avoid material expansion on account of heating. The vessel also has a centre or side mounted rotating agitation system, preferably an upward rotating auger screw or a pitched blade turbine that enables axial and radial mixing. This agitator avoids turbulent flow and thereby any undue entrapment of air in the bulk. The vessel also has jacketed heating and cooling arrangement to regulate the temperature in the bulk, with a provision to go up to at least 100° C.

A typical soap crutcher that is used for saponification, can also be used as a mixing vessel for all the other ingredients to prepare the melt for the aerated soap, prior to aeration.

In a typical aeration process, air is sparged into the molten mass, but other known means of introducing air may also be used. The air pressure in the sparger should preferably be maintained sufficiently high, so that air is able to enter into and mix within the bulk of the molten soap mass. The amount of soap in the bulk molten soap mass may be regulated to attain the desired density. It is also preferred to have a means of shearing the molten aerated mass in a way that the air bubbles can be uniformly distributed without significant variation in their size. In a preferred process, when any part of the bulk is cooled and its density measured, it should be ±0.2 $g/cm^3$ of the desired value. For such results, it is preferred to have a devoted high shear homogenization equipment, connected inline or in the bulk of the molten mass.

The final step is to cool the aerated molten soap mass. Any suitable means of cooling may be used. The aerated molten soap mass can be spread out to increase its surface area and cooled by convection or conduction. Convective cooling can be done by flowing air along the exposed surface of the mass.

Lower temperatures, e.g. 0 to 10° C. may help speed up the cooling process. Ambient air may also be used. When conduction is used, the molten aerated soap mass is poured across a conducting surface, such as a metal. A cooling medium, such as water at about 10° C., is made to flow in contact with the conducting surface on the opposite side of the mass.

Finally, the soap bars are cooled below 40° C. to enable solidification.

The distribution of air bubbles in the soap bars may be studied by Scanning Electron Microscopic. In such cases, the samples should be prepared carefully, so as to minimize damage to the microstructure of the bars. Liquid Nitrogen may be used to reduce the damage.

The invention will now be demonstrated with non-limiting examples.

EXAMPLES

Example 1

Making Preferred Aerated Soap Bars

The formulation of preferred aerated soap bars is shown in Table 1.

TABLE 1

| Ingredient | wt % |
|---|---|
| soap* | 40 |
| water | 30 |
| sodium chloride | 1.5 |
| glycerol | 14 |
| perfume | 0.5 |
| CARBOPOL ® Aqua SF | 0.1 |
| talc | 5 |
| sodium lauryl sulphate | 4 |
| stearic acid | 2 |
| others including minors | To 100 |

Note:
In table 1, *the soap was a 20:80 mixture of sodium palm kernelate and sodium palmate. The soap had 82% of the mixture, 1% sodium chloride and 17% water (moisture).

The process was as follows:

Soap was taken in a 100 kg operational capacity cylindrical dished end mixing vessel with a top mounted auger screw mixing head. The vessel was regulated for heating with steam so that the temperature of the mass could be maintained above 85° C. The pressure of compressed and filtered air was 3 bar.

The flow rate of air was matched to that of the soap mass, at about 100 $cm^3$/hour volumetric feed rate.

The agitation system was started and 40 parts of the soap were added to the vessel. Steam was circulated in the jacket of the vessel so that the soap attained temperature of around 85° C. This produced molten soap mass. This was mixed for about 1 hour. Next 30 parts water was added and the watery mass was mixed for 5 minutes. Temperature of the mixture was maintained at 85° C. Thereafter 14 parts glycerol was added to the molten soap mass and mixed for 5 minutes. Temperature of the molten soap mass was maintained at 85° C., and 4 parts sodium lauryl sulphate powder was added. The molten mass was mixed for 10 minutes. Thereafter 5 parts talc was added and the mixture was agitated for 5 minutes, followed by 1.5 parts sodium chloride. The molten mass was mixed for 2 more minutes. Finally 0.5 part perfume and 0.1 parts CARBOPOL® Aqua SF was added. The molten mass was mixed for 2 minutes and the mixing was stopped.

The mass was spread out on metallic trays of 5 cm depth. The molten soap mass was then left to cool under ambient conditions. Rectangular soap bars were then cut from the solidified bulk.

Density of the soap bars was 0.8 $g/cm^3$.

The mechanical strength and other physical properties of the preferred aerated soap bars of Table 1 were tested. The test methods were as follows:

Testing the Rate of Wear

Four pre-weighed soap bars were placed on soap trays. Two types of soap trays were used; one that has drainers or raised grids so that any water adhering to the bars may be drained away. The other types have no drainers so that water can be added to the tray to allow the bars to become "waterlogged". The procedure for measuring rate of wear was followed with both types of trays.

10 ml distilled water was added into the un-drained tray at 25° C. A washing bowl was filled with about five liters water at 25° C. The soap bars were marked on the top surface for ease of identification. The bars were immersed in water and twisted fifteen times (180° each time). This step was repeated. The bars were immersed for some more time to remove any adhering lather. Each bar was then placed back on its soap tray, ensuring that the opposite face was uppermost (i.e. the unmarked face).

The above procedure was carried out six times a day for four consecutive days, at evenly spaced intervals during each day. Alternate face of each soap bar was placed in the downward position (facing the bottom of the tray) after each washdown. Between washdowns, the soap trays were left on an open bench or draining board, under ambient conditions. After each washdown cycle, the position of each soap tray/bar was changed to minimize variability in drying conditions. At the end of each day, each of the soap trays with drainer was rinsed and dried. Soap trays without drainers were refilled with 10 ml distilled water. After the last washdown ($4^{th}$ day), all soap trays were rinsed and dried. Each washed bar was placed in its tray and allowed to dry for up to a period of nine days. On the afternoon of the $5^{th}$ day, the samples were turned so that both sides of the bar could dry. On the $8^{th}$ day, each tablet was weighed.

The rate of wear is defined as the percent weight loss as follows: (average of drained trays and trays with drainers)

$$\% \text{ wear} = \frac{(\text{initial weight} - \text{final weight}) \times 100}{\text{initial weight}}$$

Testing the Mush of Bars

Mush is a paste or gel of soap and water which is formed when soap bars are left in contact with water as in a soap-dish. Soluble components of the soap dissolve and water is absorbed into the remaining solid soap causing swelling, and for most soap, also recrystallization.

The nature of mush depends on the balance of these solution and absorption actions. Presence of a high level of mush is undesirable not only because it imparts an unpleasant feel and appearance to the soap, but also especially because the mush may separate from the bars, leaving a mess on the wash basin. Residual mush or soap residue is a known consumer negative.

The mush immersion test gives a numerical value for the amount of mush formed on a bar. The test is carried out as follows:

Rectangular bars of suitable size are taken. The width and depth of each bar is measured accurately. A line is drawn across the bar 5 cm from the bottom of the bar. This line represents the immersion depth. The bar is attached to a sample holder and suspended in an empty beaker. De-mineralised (or distilled) water at 20° C. is added to the beaker until the water level reaches the 5 cm mark on the bar. The beaker is placed in a water bath at 20° C. and left for two hours.

The soap holder and the bar is removed, the water emptied from the beaker, and the soap-holder and bar is replaced on the beaker for one minute so that excess water can drain off. Extraneous water is shaken off, the bar is removed from the soap-holder, and the weight of the bar standing it on its dry end is recorded ($W_M$).

All the mush from all 5 faces of the bar is carefully scraped off, and any remaining trace of mush is removed by wiping gently with a tissue. The weight of the bar within 5 minutes of scraping is recorded (Wr).

The quantitative amount of mush is calculated as follows:

$$\text{Mush (g/50 cm}^2) = \frac{W_M - W_r}{A} \times 50$$

where A is the surface area the bar initially immersed and in contact with water.

Testing Air Incorporation

This is measured on a scale of 1 to 5, with higher score indicating better or easier air incorporation. The scale is an indication of the time taken to increase the volume of the molten mass during processing. The scores have been explained in Table 2.

TABLE 2

| | |
|---|---|
| 1 | It takes 8 to10 minutes to see the increase in volume of the melt |
| 2 | 7 to 8 minutes |
| 3 | 5 to 7 minutes |
| 4 | 3 to 5 minutes |
| 5 | less than 3 minutes |

Testing Air Retention

Air retention is measured on a scale of 1 to 5 with higher score indicating higher air retention in the molten mass. Aeration results into an increase in volume of the molten mass. Volume of aerated molten mass is measured initially (t=1 minute) and finally (after t=10 minutes). The percentage air retention is calculated as:

$$100 \times \frac{\text{(initial volume of aerated melt} - \text{volume of un-aerated melt)}}{\text{(final volume of aerated melt} - \text{volume of un-aerated melt)}}$$

The scores have been explained in Table 3.

TABLE 3

| | |
|---|---|
| 1 | air retention 10% |
| 2 | 11 to 20% |
| 3 | 21 to 30% |
| 4 | 31 to 40% |
| 5 | greater than 41% |

Example 2

Effect of the Acrylate Polymer

Base (control) soap bars were made by the process already described. The formulation of the control bars was identical to that of Table 1, except that the control bars did not have CARBOPOL™ Aqua SF. Various preferred aerated soap bars were made by changing the amount of CARBOPOL™ Aqua SF. This was adjusted by appropriately changing the amount of water. The rate of wear, mush, air incorporation, air retention and density of these bars were measured. Results are shown in Table 4.

TABLE 4

| polymer/ wt % | rate of wear (%) | Mush (g/50 cm$^2$) | air incorporation | air retention | density (g/cm$^3$) |
|---|---|---|---|---|---|
| 0.00 | 65.3 | 9.37 | 2 | 1 | 0.94 |
| 0.15 | 64.5 | 4.37 | 5 | 4 | 0.66 |
| 0.30 | 62.4 | 4.62 | 4 | 3 | 0.77 |
| 0.60 | 60.7 | 4.55 | 4 | 3 | 0.79 |
| 1.00 | 50.2 | 6.3 | 3 | 3 | 0.75 |
| 3.00 | 44.3 | 9.21 | 2 | 3 | 0.78 |

The data in Table 4 indicates that preferred aerated soap bars with 0.15 to 3 wt % CARBOPOL™ Aqua SF had better air retention and lower density. Air incorporation and rate of wear was particularly good when the polymer was 1 to 3 wt %. Similarly mush values were lower when the polymer was 0.15 to 1 wt %.

Example 3

Effect of the Polyol

Base (control) soap bars were made by the process already described. The formulation of the control bars was identical to that of Table 1, except that the control bars did not have any polyol. Various preferred aerated soap bars were made by changing the amount of glycerol.

This was adjusted by appropriately changing the amount of water. One preferred soap bar was made with 15% sorbitol, instead of 15% glycerol. The rate of wear, mush, air incorporation, air retention and density of these bars were measured. Results are shown in table 5.

TABLE 5

| Polyol/wt % | rate of wear (%) | mush (g/50 cm$^2$) | air incorporation | air retention | density (g/cm$^3$) |
|---|---|---|---|---|---|
| 0 | not measurable | not measurable | 3 | 2 | not measurable |
| 5 | 55.9 | 3.07 | 5 | 4 | 0.68 |
| 10 | 60.2 | 4 | 5 | 4 | 0.65 |
| 15 | 63.5 | 4.6 | 5 | 4 | 0.65 |
| 15 (Sorbitol) | 60 | 4.6 | 5 | 4 | 0.65 |
| 30 | 77.6 | 6.2 | 5 | 3 | 0.78 |
| 40 | 80.5 | 9 | 4 | 3 | 0.75 |

The data in table 5 indicate that polyol (glycerol or sorbitol) provides improves air incorporation, air retention, mush and rate of wear. Polyol lesser than 40 wt % provides better air incorporation and further reduced levels provide even better air retention.

Example 4

Effect of Water

The level of water was adjusted by varying the soap and polyol. The rate of wear, mush, air incorporation, air retention and density of these bars were measured. Results are shown in Table 6.

TABLE 6

| level of water wt % | rate of wear (%) | mush ($g/50\ cm^2$) | air incorporation | air retention | density ($g/cm^3$) |
|---|---|---|---|---|---|
| 20 | 62.1 | 5 | 2 | 4 | 0.68 |
| 30 | 64.5 | 4.37 | 5 | 4 | 0.68 |
| 40 | 64.2 | 4.2 | 5 | 3 | 0.75 |
| 50 | 68.9 | 5.6 | 3 | 2 | 0.87 |

The data indicates that bars with greater than 20% water, but less than 50% water had better air retention and air incorporation. Bars with more than 50 wt % water could not be made as the molten mass had very low viscosity.

Example 5

Effect of Electrolyte

Preferred aerated soap bars were made by varying the amount of sodium chloride in the formulation of Table 1. The level of sodium chloride was adjusted by varying the water content. The rate of wear, mush, air incorporation, air retention and density of these bars were measured. Results are shown in Table 7.

TABLE 7

| level of electrolyte wt % | rate of wear (%) | mush ($g/50\ cm^2$) | air incorporation | air retention | density ($g/cm^3$) |
|---|---|---|---|---|---|
| 0 | Not measured | not measured | not measured | not measured | not measured |
| 0.6 | 61.5 | 2.8 | 5 | 2 | 0.85 |
| 1.6 | 53.9 | 2.45 | 5 | 4 | 0.7 |
| 2.1 | 52.6 | 2.3 | 5 | 4 | 0.68 |
| 3.6 | 50.3 | 2.2 | 5 | 4 | 0.66 |

Without the electrolyte, the bars could not be formed.

The data in Table 7 indicates that an electrolyte is essential to form bars. In particular, electrolyte greater than 0.6% provides better air retention, air incorporation and lower rate of wear, with lower density.

Example 6

Effect of Organic Material and Inorganic Particulate Material

Preferred aerated soap bars with varying levels of talc and starch were prepared. The formulations were balanced by varying the amount of soap and water. The rate of wear, mush, air incorporation, air retention and density of these bars were measured. Results are shown in Table 8.

TABLE 8

| talc wt % | starch wt % | rate of wear (%) | mush ($g/50\ cm^2$) | lather (ml) | air incorporation | air retention | density ($g/cm^3$) |
|---|---|---|---|---|---|---|---|
| 0 | 0 | 55 | 8.5 | 220 | 3 | 3 | 0.8 |
| 5 | 0 | 64.76 | 4.13 | 190 | 3 | 3 | 0.82 |
| 5 | 5 | 65.25 | 4.09 | 192 | 3 | 3 | 0.85 |
| 5 | 15 | 61.43 | 4.08 | 200 | 3 | 5 | 0.72 |
| 5 | 20 | 60.44 | 7.45 | 167 | 3 | 5 | 0.82 |
| 5 | 30 | 76.63 | 4.97 | 179 | 4 | 5 | 0.95 |
| 30 | 10 | 67.13 | 4.2 | 196 | 3 | 5 | 0.93 |

The data in Table 8 indicates that talc and starch improves mush, without adversely affecting air incorporation. In particular, talc and starch at ratios from 1:1 to 1:6 improves air retention. In bars where the air retention was higher, the mush was much lower.

Example 7

Preferred Aerated Soap Bars with Cellulose Ether

Preferred aerated soap bars having cellulose ether (sodium carboxymethyl cellulose), instead of acrylate polymer were made. The formulation of these bars is shown in Table 9.

TABLE 9

| Ingredient | wt % |
|---|---|
| soap* | 40 |
| water | 32 |
| sodium chloride | 1.5 |
| glycerol | 14 |
| perfume | 0.5 |
| sodium carboxymethyl cellulose | 0.5 |
| talc | 5 |
| sodium lauryl sulphate | 4 |
| stearic acid | 2 |
| others including minors | To 100 |

The aerated soap bars were found to have better air retention and lower density, better air incorporation score and lower rate of wear. Density of the bars was 0.8 $g/cm^3$.

In a third aspect the invention provides use of aerated soap bars of the first aspect.

It will be appreciated that the illustrated examples provide for aerated soap bars having acrylates or cellulose ethers. The bars have lower rate of wear, lower mush and lower density; and higher air incorporation and air retention.

It should be understood that the specific forms of the invention herein illustrated and described are intended to be representative only as certain changes may be made therein without departing from the clear teachings of the disclosure.

Although the invention has been described with reference to specific embodiments, it will be appreciated by those skilled in the art that the invention may be embodied in many other forms.

The invention claimed is:

1. Aerated soap bar having a density from 0.2 to 0.99 $g/cm^3$, comprising:

(i) 20 to 80 wt % soap;

(ii) 2 to 40 wt % polyol;

(iii) 5 to 50% water; and, (iv) 0.5 to 5 wt % electrolyte;

wherein said bar comprises 0.1 to 5 wt % acrylates.

2. Aerated soap bar as claimed in claim 1 comprising 1 to 50 wt % inorganic particulate material, wherein said inorganic particulate material is selected from talc, calcium carbonate, magnesium carbonate, clays and mixtures thereof.

3. Aerated soap bar as claimed in claim 1 comprising 0.1 to 40 wt % organic material selected from starch, cellulose, or wax.

4. Aerated soap bar as claimed in claim 2 wherein the bar comprises talc and starch.

5. Aerated soap bar as claimed in claim 4 wherein ratio of talc to starch is from 1:1 to 1:6.

6. Aerated soap bar as claimed in claim 1 comprising 0.1 to 10 wt % fatty acids.

7. Aerated soap bar as claimed in claim 1 comprising 1 to 30 wt % non-soap surfactant selected from non-ionic, anionic, cationic or zwitterionic surfactants, or a mixture thereof.

8. A process of preparing aerated soap bars, said process comprising the steps of:

(i) mixing 20 to 80 parts soap, 2 to 40 parts polyol, 5 to 50 parts water, 0.5 to 5 parts electrolyte, and 0.1 to 5 parts acrylates, to obtain a mixture;

(ii) heating said mixture to 50 to 95° C. to obtain a molten soap mass;

(iii) aerating said molten soap mass; and, (iv) cooling the aerated molten soap mass to obtain aerated soap bars having density from 0.2 to 0.99 g/$cm^3$.

9. A process as claimed in claim 8 wherein the molten soap mass is stored in a container, and a part of the molten soap mass is pumped out and aerated.

10. A process as claimed in claim 9 wherein the aerated molten soap mass is mixed in a homogenizer, and returned to the container, or another container.

* * * * *